United States Patent [19]
Mers Kelly et al.

[11] Patent Number: 6,036,717
[45] Date of Patent: Mar. 14, 2000

[54] EMBOLECTOMY CATHETER

[75] Inventors: William C. Mers Kelly, Xenia, Ohio; David Y. Phelps, Louisville, Ky.

[73] Assignee: Louisville Laboratories, Inc., Louisville, Ky.

[21] Appl. No.: 09/103,211

[22] Filed: Jun. 23, 1998

Related U.S. Application Data

[63] Continuation of application No. 08/813,798, Mar. 6, 1997, Pat. No. 5,769,871, and a continuation of application No. 08/559,157, Nov. 17, 1995, abandoned.

[51] Int. Cl.[7] .................................................. A61M 29/00
[52] U.S. Cl. ........................ 606/200; 606/159; 606/108
[58] Field of Search .................................... 606/108, 191, 606/198, 199, 200, 159

[56] References Cited

U.S. PATENT DOCUMENTS

| | | | |
|---|---|---|---|
| 5,370,657 | 12/1994 | Irie | 606/200 |
| 5,375,612 | 12/1994 | Cottenceau et al. | 606/191 |
| 5,571,122 | 11/1996 | Kelly et al. | 606/159 |
| 5,713,907 | 2/1998 | Hogendijk et al. | 606/198 |

*Primary Examiner*—Michael Buiz
*Assistant Examiner*—Daphna Shai
*Attorney, Agent, or Firm*—Don Halgren

[57] ABSTRACT

The present invention comprises an embolectomy catheter for the removal of an embolus within a vessel of a patient, including a catheter shaft having a distal end with a diametrically adjustable hinged compartment thereat. The catheter shaft has a proximal end with a handle attached thereon. A longitudinally displaceable cannula is connected to the distal end of the catheter shaft and to a slidable tab in the handle, to permit controlled adjustment of the diametric size of the hinged compartment arranged adjacent the distal end of the catheter when the slidable tab is moved relative to the handle, to allow a physician to open the compartment to any desired size relative to a patient's vessel. The compartment may then be pulled through the vessel via a pull on the handle, to collect any embolus therewithin.

17 Claims, 2 Drawing Sheets

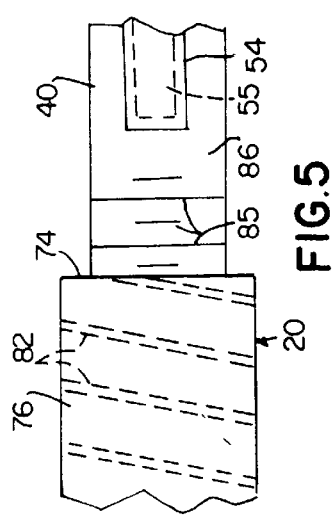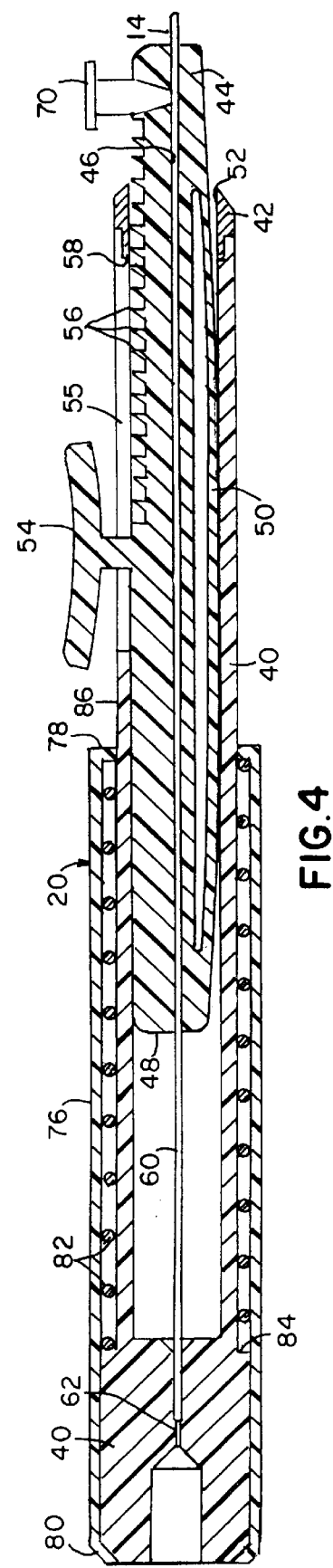

EMBOLECTOMY CATHETER

This is a continuation of co-pending application Ser. No. 08/813,748 filed on Mar. 6, 1997 now U.S. Pat. No. 5,769,871 and Ser. No. 08/559,157, filed on Nov. 17, 1995, now abandoned.

BACKGROUND OF THE INVENTION

(1) Field of the Invention

The present invention relates to the field of medical devices, and more particularly, to a catheter device for performing embolectomies.

(2) Prior Art

A thrombus is a clot of blood formed within a blood vessel and which remains attached to its place of origin. An embolism is the obstruction of a blood vessel by a foreign or abnormal particle. The occasion of such a thrombosis or embolism within hospitalized patients, are one of their leading causes of death.

A number of different embolus extraction devices have been proposed over the past few years. U.S. Pat. No. 4,406,671 to Weinrib, shows a catheter with a coiled tip section which is arranged for insertion into a blood vessel. This coil is linearly stretchable, so as to minimize its outside diameter, and when pulled proximally, through an embolus, is expected to scoop clot material from the blood vessel.

A further device is shown in U.S. Pat. No. 4,762,130 to Fogarty et al., showing a catheter with a corkscrew-like balloon. Removal of the inflated balloon is supposed to remove clot material from the blood vessel within which the helical balloon resides.

A further balloon catheter device is shown in U.S. Pat. No. 5,112,347 to Taheri which discloses an embolectomy catheter having a balloon on its distal end. A plurality of circumferentially disposed fingers are spaced within the balloon, each finger having a proximal end. This end, when the balloon is deflated, defines a proximally extending scoop, which during the withdrawal thereof, captures embolii therewithin.

It is an object of the present invention, to provide an embolectomy catheter which does not utilize a balloon for the retrieval of material from within the blood vessel.

It is a further object of the invention, to provide an embolectomy catheter which is discernibly adjustable in diameter so as to permit utilization in a variety of vessel sizes.

It is yet a further object of the present invention, to provide an embolectomy catheter, which permits the distribution of medicaments before, during or after removal of any clots from a vessel.

BRIEF SUMMARY OF THE INVENTION

The present invention comprises an embolectomy catheter, utilizable for the removal of an embolus from a body artery or vein. Such a catheter is comprised of an elongated hollow shaft, having a distal end and a proximal end which comprises a handle. The catheter shaft extending distally from the handle is made from a polymeric material. A hingedly flexible annular compartment is disposed adjacent the distal end of the catheter shaft. A flexible hollow polymeric tip is disposed distally off the hingedly flexible member, and comprises the distalmost end. The distalmost tip may have a plurality of medicament discharge orifices arranged thereabout.

The hingedly flexible compartment is co-axial with the catheter shaft, and is attached by a bonding to the distal end thereof, the distal hollow tip of the catheter shaft, being bonded to the distal end of the hingedly flexible compartment. An annular groove is disposed at a longitudinal midpoint of the hinged flexible compartment, to permit flexing thereat. The hinged flexible compartment is made of a porous yet relatively rigid material, such as a woven polymer or nylon, which defines two articulable annular surfaces connected to one another and at their respective ends, to the catheter shaft by their annular flex joints. The polymeric catheter shaft has a proximal end, which is attached to the adjustment handle at the proximal end of embolectomy catheter.

The adjustment handle comprises an elongated, generally hollow housing having a distal end which slidingly receives a shaft support member. The shaft support member has a bore extending longitudinally therethrough. The catheter shaft extends within that longitudinal bore to the proximal end of the shaft Support member. The shaft support member has a spaced apart bow portion which frictionally engages a first inner wall of the hollow elongated housing. Opposite the bow portion on the shaft support member, there is a thumb rest. The thumb rest is utilized to permit adjustment of the shaft support member within the hollow elongated housing. A plurality of serrations are longitudinally disposed on the shaft support member adjacent to the thumb pad. A serration engaging tooth is disposed at the distal end of the hollow elongated housing, to engage the serration on the shaft support member.

An innermost shaft extends from the distal most tip of the flexible hollow tip on the distal end of the catheter, where it is bonded thereto, through the hollow shaft of the catheter, and through the hollow elongated housing, beyond its proximal most end, and is secured into a stepped central bore at the proximal end of the elongated housing. The elongated bore at the proximal end of the hollow elongated housing is open at the proximal end thereof.

There is a luer fitting disposed at the distal end of the shaft support member, which luer member is in fluid communication with an annular space between the inner shaft and the outer shaft of the catheter, distally of the handle.

A force gauge is disposed about the proximalmost half of the adjustment handle. The force gauge comprises a hollow barrel shaped member having a distalmost flange which engages the outer surface of the shaft support member. The proximal end of the barrel has a flange which overlaps the proximal end of hollow elongated housing. A compression spring is disposed between the barrel and the hollow elongated housing. The distalmost end of the compression spring mates against the flange on the distal end of the barrel. The proximal end of the compression spring mates against a shoulder disposed on the outer surface of the proximal end of the elongated housing.

A series of force unit calibrations are marked onto the outermost surface of the hollow elongated housing, radially inwardly over the distalmost end of the barrel. The barrel is biasedly moveable with respect to the elongated housing.

In an embolectomy or thrombolectomy procedure, a catheter is inserted into a body vessel with the hingedly flexible annular compartment in its normal configuration, that is, with its walls coaxial with the adjacent shaft. When it is desired to perform an embolectomy procedure, the operating physician presses against the thumb pad, so as to compress the bow portion thus moving the serration away from the serration locking point at the distal end of the hollow elongated housing. Simultaneously with the biasing of the bow portion of the shaft support member, the thumb pad and shaft support member are thus pushed distally away from the (adjustment handle by the operating physician, so as to cause a forward motion within the catheter (outer) shaft. The distalmost end of the catheter shaft however, is anchored by the inner shaft, to the proximalmost end of the adjustment handle, so that the compression forces in the outer shaft, (and tension in the inner shaft) thereby affects a bulging at the annular hindgepoint at the hingedly flexible compartment at the distal end of the catheter shaft. By a step-wise distal motion of the shaft support member, the operating physician can thus correspondingly increase the diameter of the hingedly flexible compartment or decrease the diameter of the hingedly flexible compartment by retraction of the shaft support member within the hollow elongated housing, so as to have a correspondence between the outer diameter of the hingedly flexible compartment and the inner diameter of the body vessel being cleared.

Upon reaching the appropriate respective diameter of the hingedly flexible compartment, the shaft support member may be locked by its serration, engaging with the serration lock point to permit the operating physician to pull the handle assembly proximally, thus clearing the body vessel of undesired material. By holding onto the barrel at the proximalmost end of the adjustment handle, the force gauge is thus utilized to expose the rearward pull forces being utilized within the body vessel. Limitations may thus be applied so as to not exceed certain limits within any particular body vessel.

The innermost shaft which has a distal end which is bonded to the distal end of the catheter tip, is in communication with a distal orifice within the hollow tip thereof. The orifice in the hollow tip permits a guide wire to extend through the bore in the proximalmost end of the handle, through the innermost shaft, and out through the hollow tip of the catheter. The bore at the hollow flexible tip, also permits medicaments to be dispersed therefrom, such medicaments comprising heparin, dyes, or renographins, as the catheter assembly is being moved through a body vessel.

The invention thus comprises an embolectomy catheter for the removal of an embolus within a vessel of a patient, comprising a catheter shaft having a distal end with a diametrically adjustable hinged compartment thereat, the catheter shaft having a proximal end, a handle attached to the proximal end of the shaft, and a means for adjusting the diametric size of the hinged compartment arranged between the distal end of the catheter, and the handle. The handle also has a force sensing gauge thereon, to permit the amount of pull force being applied to the hinged compartment to be noted when pull tension is applied to the handle. The means for adjusting the diametric size of the hinged compartment includes an inner shaft, the inner shaft having a distal end which is attached to the distalmost end of the catheter shaft, the inner shaft having a proximal end which is attached to the handle to permit tension to be applied to the inner shaft, and hence to effect diametric change to the hinged compartment. The inner shaft is hollow, and the distal tip of the catheter shaft has a distal orifice thereat, the hollow inner shaft and the distal orifice being a communication with one another to permit a guide wire or medicaments to flow therethrough. An annular passageway is disposed between the inner shaft and the catheter shaft, to permit medicaments to be transmitted from a valve in the handle, to a discharge orifice in or adjacent to the hinged compartment in the catheter shaft. The proximal end of the catheter shaft is attached to a longitudinally movable support member arranged in the handle. The support member has serrations on one side thereof to permit the support member to locked into a longitudinally fixed position with respect to the handle, thus locking into position the diametrically adjustable hinged compartment.

The embolectomy catheter may have a radiopaque marker band arranged distally of the hinged compartment to permit fluoroscopic locating and positioning of the hinged compartment. It may have a radiopaque marker band arranged proximally adjacent the hinged compartment to permit fluoroscopic locating and positioning of the distal tip of the catheter, and the catheter may have a radiopaque marker band arranged both proximally and distally of the hinged compartment to permit fluoroscopic confirmation of the diametric adjustment of the hinged compartment.

The force sensing gauge includes a housing having indicators marked thereon, and a barrel member is movably arranged about the housing wherein movement of the barrel member with respect to the housing permits indicators to be displayed indicating the amount of force pulling longitudinally on the handle, and hence the amount of force pulling longitudinally on the catheter shaft and hence the hinged compartment. A spring is arranged between the housing and the barrel member to provide a bias therebetween. The support member has a bias member on one longitudinal side thereof, to permit the serrations on the support member to fixedly engage the handle.

The invention also includes a method for performing an embolectomy procedure so as to remove an embolus from the vessel of a patient, comprising the steps of threading the distal end of an embolectomy catheter onto the guide wire and into the vessel of the patient, beyond the site of the embolus, the embolectomy catheter having a hinged compartment on its distal end, the embolectomy catheter having a proximal end with an adjustment means in a handle therein, positioning the adjustment means in the handle, so as to adjust the diameter of the hinged compartment to be compatible with the diameter of the vessel being treated, and withdrawing the catheter from the vessel by pulling longitudinally on the handle, to effect capture and removal of any emboli from the vessel by the diametrically expanded hinged compartment. The method includes the step of injecting a medicament in the handle so as to be transmitted through the catheter and out a distal orifice thereof and into the vessel being treated.

BRIEF DESCRIPTIONS OF THE DRAWINGS

The objects and advantages of the present invention will became more apparent, when used in conjunction with the following drawings, in which:

FIG. 4 is a side elevational view, in section, showing the adjustment handle of the present invention; and FIG. 5 is a plan view of a portion of the adjustment handle taken along the lines A—A of FIG. 4.

DESCRIPTION OF THE PREFERRED EMBODIMENTS

Figure 1:
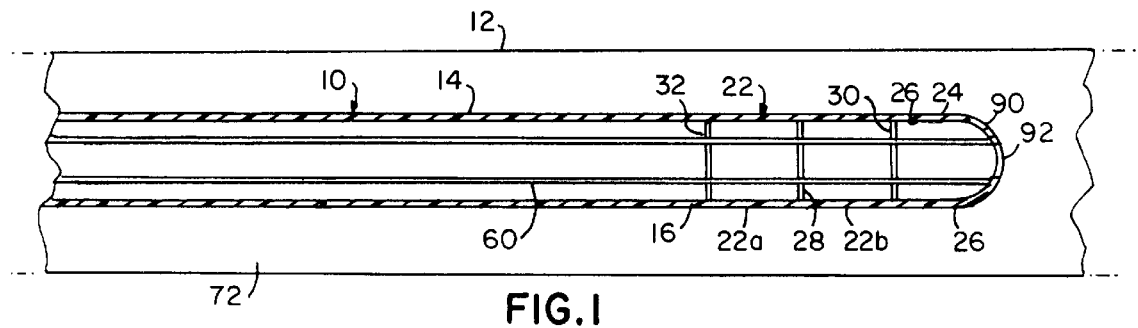
FIG. 1 is a side elevational view, taken in section, of the catheter shaft portion of the device of the present invention.
Figure 2:
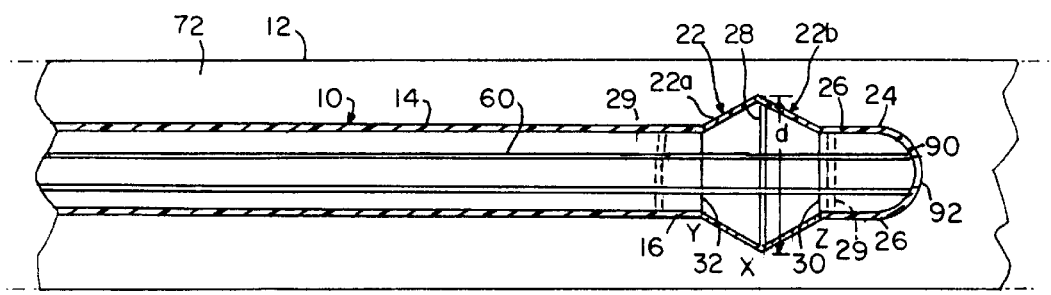
FIG. 2 is the catheter shaft of FIG. 1, at a mid point in its operational configuration.
Figure 3:
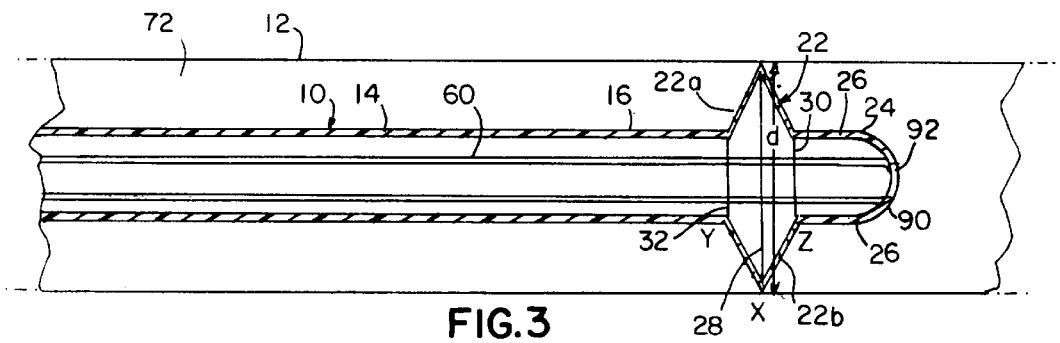
FIG. 3 is a view similar to FIG. 2, with its full diameter being utilized.

The present invention comprises an embolectomy catheter 10, utilizable for the removal of foreign material from a body artery or vein 12. Such a catheter is comprised of an elongated hollow shaft 14, having a distal end 16, that is shown in FIGS. 1, 2 and 3, and a proximal end comprising a handle 20, as shown in FIG. 4. The catheter shaft 14 extending distally from the handle 20 is made from a polymeric material. A hingedly flexible annular compartment 22. shown in FIGS. 1–3, is disposed adjacent the distal end 16 of the catheter shaft 14. A flexible hollow polymeric tip 24 is disposed distally off of the hingedly flexible compartment 22, and comprises the distalmost end. The distant most tip 24 may have a plurality of medicament discharge orifices arranged 26 thereabout. The hinged compartment 22 is of triangular shape in cross section, when appropriately actuated, as may be seen by the points x, y and z, in FIGS. 2 and 3, respectively.

The hingedly flexible compartment 22 is co-axial with the catheter shaft 14, and is attached by a bonding to the distal end thereof, the distal hollow tip 24 of the catheter shaft 12 being bonded to the distal end of the hingedly flexible compartment 22. An annular groove 28 is disposed at a longitudinal midpoint of the hinged flexible compartment 22, to permit flexing along that annular locus. The hinged flexible compartment 22 is thus made of a pair of porous annular bands 22a and 22b, of relatively rigid material, such as a woven polymer or nylon, and is bendable at its central annular groove 28 and distal and proximal annular joints 30 and 32. Thus, the hinged compartment 22 is comprised of two relatively rigid annular surfaces 22a and 22b, each of which are connected by their "living" hinge defined by the groove 28 and at their annular hinges 30 and 32. The length of the sides x & y and x & z remain the same, but the angle yxz changes to effectuate diameter changes across the width of the compartment 22 when an inner shaft described hereinbelow, is adjustably moved in the handle 20. The polymeric catheter shaft has a proximal end, which is attached to the adjustment handle 20 at the proximal end of embolectomy catheter 10. A radiopaque marker band 29 may be disposed distally and/or proximally of the compartment 22 to facilitate fluoroscopic location and placement of the compartment 22 within a body vessel 12. Such a pair of bands 29 may also be utilized to confirm adjustment (contraction/elongation) of the hinged compartment 22, by the bands 29 being closer or further apart from one another when utilized as a pair.

The adjustment handle 20 comprises an elongated, generally hollow housing 40, as shown in FIG. 4, having a distal end 42 which slidingly receives a shaft support member 44. The shaft support member 44 has a bore 46 extending longitudinally therethrough. The catheter shaft 14 extends within that longitudinal bore 46 to the proximal end 48 of the shaft support member 44. The shaft support member 44 has a spaced apart bow 50 which frictionally engages a first inner wall 52 of the hollow elongated housing 40. Opposite the bow 50 on the shaft support member 44, is a thumb rest 54. The thumb rest 54 is utilized to permit adjustment of the shaft support member 44 within the hollow elongated housing 40. The thumb rest 54 is permitted to slide within a slot 55 within the housing 40. A plurality of serrations 56 are longitudinally disposed on the shaft support member 44 adjacent to the thumb pad 54. A serration engaging tooth 58 is disposed at the distal end of the hollow elongated housing 40, to engage the serrations 56 on the shaft support member 44, as shown in FIG. 4.

An inner shaft 60 extends from the distalmost tip 24 of the flexible hollow tip on the distal end of the catheter 14, which is bonded thereto through the hollow shaft 14 of the catheter, and through the hollow elongated housing 46, beyond its proximalmost end 48, and is secured into a stepped central bore 62 at the proximal end of the elongated housing 40. The elongated central bore 62 at the proximal end of the hollow elongated housing 40, is open at the proximal end thereof.

There is a luer fitting 70 disposed at the distal end of the shaft support member 44, which luer fitting 70 is in fluid communication with an annular space 72 between the inner shaft 60 and the outer shaft 14 of the catheter 10 distally of the handle 20.

A force gauge 74 is disposed about the proximal most half of the adjustment handle 20. The force gauge 74 comprises a hollow barrel shaped member 76 having a distalmost flange 78 which engages the outer surface of the housing 40. The proximal end of the barrel member 76 has a flange 80 which overlaps the proximal end of hollow elongated housing 40. A compression spring 82 is disposed between the barrel member 76 and the hollow elongated housing 40. The distalmost end of the compression spring 82 mates against the flange 78 on the distal end of the barrel member 76. The proximal end of the compression spring 82 mates against a shoulder 84 disposed on the outer surface of the proximal end of the elongated housing 40.

A series of force unit calibrations 85 are marked onto the outer most surface 86 of the hollow elongated housing 40, radially inwardly over the distalmost end of the barrel member 76. The barrel member 76 is biasedly moveable with respect to the elongated housing 40.

In an embolectomy or thrombectomy procedure, a catheter 10 is inserted into a body vessel 12 with the hingedly flexible annular compartment 22 in its normal configuration, that is, with its walls coaxial with the adjacent shaft 14, as shown in FIG. 1. When it is desired to perform an embolectomy procedure, the operating physician presses against the thumb pad 54, so as to compress the bow 50 thus moving the serrations 56 radially away from the serration locking point 58 at the distal end of the hollow elongated housing 40. Simultaneously with the biasing of the bow 50 of the shaft support member 44, the thumb pad 54 and shaft support member 44 are thus pushed distally away from the adjustment handle 20, so as to cause a forward (distal) motion within the catheter shaft 14. The distalmost end 16 of the catheter shaft 14 however, is anchored to the adjustment handle 44, so that the compression forces within the catheter shaft 14 thereby effects a bulging at the annular hingepoint groove 28, at the hingedly flexible compartment 22 at the distal end of the catheter shaft 10, as shown in FIGS. 2 and 3. By a step-wise distally-directed motion of the shaft support member 44, the operating physician can correspondingly increase the diameter of the hingedly flexible compartment 22 or can decrease the diameter of the hingedly flexible compartment 22 by retraction of the shaft support member 44 within the hollow elongated housing 40 so as to have a proportional correspondence between the outer diameter "d" of the hingedly flexible compartment 22 and the inner diameter of the body vessel 12 being cleared.

Upon reaching the appropriate respective diameter of the hingedly flexible compartment 22, the shaft support member 44 may locked by its serration 56, engaging with the serration lock point 58 to permit the operating physician to pull the handle assembly 20 proximally (to the left as shown in FIG. 4), thus clearing the body vessel 12 of embolii. By holding onto the barrel member 76 at the proximalmost end of the adjustment handle 20, the force gauge 74 is thus utilized to expose the rearward pull forces being utilized within the body vessel. Limitations may thus be applied so as to not exceed certain limits within any particular body vessel.

The innermost shaft 60 which has a distal end which is bonded to the distal tip 90 of the catheter tip 24, is in communication with a distal orifice 92 within the hollow tip 90 thereof. The orifice 92 in the hollow tip 24 permits a guide wire (not shown) to extend through the bore 62 in the proximalmost end of the handle 20, through the innermost shaft 60 throughout the hollow tip 90 of the catheter 10. The bore 62 at the hollow, flexible tip 24, also permits medicaments to be dispersed therefrom, such medicaments comprising dyes, or renographins as the catheter assembly 10 is being moved through a body vessel 12.

We claim:

1. An embolectomy catheter for the removal of an emboli within a vessel of a patient, comprising:

a catheter shaft having a distal end with a diametrically adjustable hinged compartment thereat, said catheter shaft also having a proximal end;

a handle attached to said proximal end of said shaft, and, a means for adjusting the diametric size of said hinged compartment arranged between said distal end of said catheter, and said handle, to enable said compartment to sweep any diameter body vessel as it is pulled therewithin.

2. The embolectomy catheter as recited in claim 1, wherein said handle also has a force sensing gauge thereon, to permit the amount of pull force being applied to said hinged compartment to be noted when pull tension is applied to said handle.

3. The embolectomy catheter as recited in claim 2, wherein said force sensing gauge includes a housing having indicators marked thereon, and a barrel member which is movably arranged about said housing wherein movement of said barrel member with respect to said housing permits indicators to be displayed indicating the amount of force pulling longitudinally on said handle, and hence the amount of force pulling longitudinally on said catheter shaft and said hinged compartment in a vessel being swept clear.

4. The embolectomy catheter as recited in claim 3, wherein a spring is arranged between said housing and said barrel member to provide a bias therebetween.

5. The embolectomy catheter as recited in claim 1, wherein said means for adjusting the diametric size of said hinged compartment includes an inner shaft, said inner shaft having a distal end which is attached to the distalmost end of said catheter shaft, said inner shaft having a proximal end which is attached to said handle to permit tension to be applied to said inner shaft, and hence effect a diametric change in said hinged compartment.

6. The embolectomy catheter as recited in claim 5, wherein said inner shaft is hollow, and said distal tip of said catheter shaft has a distal orifice thereat, said hollow inner shaft and said distal orifice being in communication with one another to permit a guide wire or medicaments to flow therethrough.

7. The embolectomy catheter as recited in claim 5, wherein an annular passageway is disposed between said inner shaft and said catheter shaft, to permit medicaments to be transmitted from a valve in said handle, to a discharge orifice in or adjacent to said hinged compartment in said distal end of said catheter shaft.

8. The embolectomy catheter as recited in claim 5, wherein said proximal end of said catheter shaft is attached to a longitudinally movable support member arranged in said handle.

9. The embolectomy catheter as recited in claim 8, wherein said support member has serrations on one side thereof to permit said support member to be locked into a longitudinally fixed position with respect to said handle, thus locking into a fixed position the diametrically adjustable hinged compartment.

10. The embolectomy catheter as recited in claim 9, wherein said support member has a bias member on one longitudinal side thereof, to permit said serrations on said support member to fixedly engage said handle.

11. The embolectomy catheter as recited in claim 1, wherein said catheter has a radiopaque marker band arranged distally of said hinged compartment to permit fluoroscopic locating and positioning of said hinged compartment.

12. The embolectomy catheter as recited in claim 1, wherein said catheter has a radiopaque marker band arranged proximally adjacent said hinged compartment to permit fluoroscopic locating and positioning of the distal tip of said catheter.

13. The embolectomy catheter as recited in claim 1, wherein said catheter has a radiopaque marker band arranged both proximally and distally of said hinged compartment to permit fluoroscopic confirmation of the diametric adjustment of said hinged compartment.

14. A method for performing an embolectomy procedure so as to remove an embolus from the vessel of a patient, comprising the steps of:

threading the distal end of an embolectomy catheter directly into the vessel of the patient or onto said guide wire which has been placed in the vessel of the patient, beyond the site of the embolus, said embolectomy catheter having a hinged compartment on its distal end, said embolectomy catheter having a proximal end with an adjustment means in a handle therein;

positioning said adjustment means in said handle, so as to adjust the diameter of said hinged compartment to be compatible with the diameter of the vessel being treated; and withdrawing said catheter from the vessel by pulling longitudinally on said handle, to effect capture and removal of said embolus from the vessel by said diametrically expanded hinged compartment.

15. The method for performing an embolectomy procedure as recited in claim 14, including the step of:

injecting a medicament in a luer fitting in said handle so as to be transmitted through an annular channel in said catheter and out a distal orifice thereof and into said vessel.

16. The method for performing an embolectomy procedure as recited in claim 15, incliding the steps of:

arranging a barrel to be disposed radially about the proximal end of said handle;

securing a spring between said adjustment means and said barrel, so as to be able to meter and control the tension being applied to said hingedly adjustable compartment, when said handle is pulled proximately by pulling proximately on said barrel.

17. The method for performing an embolectomy procedure as recited in claim 16, including the step of:

applying a series of indicators on said handle so as to permit said tension to be viewed as a displacement of said barrel and said adjustment means relative to said indicators.

* * * * *